United States Patent [19]
Fahy

[11] Patent Number: 5,586,438
[45] Date of Patent: Dec. 24, 1996

[54] PORTABLE DEVICE FOR PRESERVING ORGANS BY STATIC STORAGE OR PERFUSION

[75] Inventor: Gregory M. Fahy, Gaithersburg, Md.

[73] Assignees: Organ, Inc.; LRT, Inc., both of Chicago, Ill.

[21] Appl. No.: 411,274

[22] Filed: Mar. 27, 1995

[51] Int. Cl.⁶ .................................. F24F 3/16; F25D 3/08
[52] U.S. Cl. .................................. 62/78; 62/306; 62/371; 62/457.9; 435/284.1
[58] Field of Search .................................. 62/64, 78, 306, 62/371, 372, 376, 457.1, 457.2, 457.9; 435/1.2, 284.1

[56] References Cited

U.S. PATENT DOCUMENTS

| | | | |
|---|---|---|---|
| 3,607,646 | 9/1971 | de Roissart | 62/306 X |
| 3,632,473 | 1/1972 | Belzer et al. | 62/306 X |
| 3,777,507 | 12/1973 | Burton et al. | 62/306 X |
| 3,810,367 | 5/1974 | Peterson | 62/371 X |
| 3,914,954 | 10/1975 | Doerig | 62/306 X |
| 3,995,444 | 12/1976 | Clark et al. . | |
| 4,186,565 | 2/1980 | Toledo-Pereyra | 62/306 X |
| 4,242,883 | 1/1981 | Toledo-Pereyra | 62/306 X |
| 4,462,215 | 7/1984 | Kuraoka et al. | 62/78 |
| 4,471,629 | 9/1984 | Toledo-Pereyra | 62/78 X |
| 4,474,016 | 10/1984 | Winchell | 62/371 X |
| 4,494,385 | 1/1985 | Kuraoka et al. | 62/306 X |
| 4,502,295 | 3/1985 | Toledo-Pereyra | 62/306 X |
| 4,596,250 | 6/1986 | Beisang, III et al. | 62/530 X |
| 4,723,974 | 2/1988 | Ammerman | 62/371 X |
| 4,745,759 | 5/1988 | Bauer et al. . | |
| 4,766,740 | 8/1988 | Bradley et al. | 62/457.9 X |
| 4,951,482 | 8/1990 | Gilbert | 62/306 X |
| 4,958,506 | 9/1990 | Guilhem et al. | 62/371 X |
| 5,157,930 | 10/1992 | McGhee et al. | 62/306 X |
| 5,217,860 | 6/1993 | Fahy et al. . | |
| 5,285,657 | 2/1994 | Bacchi et al. | 62/457.9 |
| 5,434,045 | 7/1995 | Jost | 62/457.1 X |

OTHER PUBLICATIONS

D. R. Wheeldon et al., "Storage and Transport of Heart and Heart–Lung Donor Organs With Inflatable Cushions and Eutectoid Cooling", Jul./Aug. 1988, vol. 7, pp. 265–268.

*Primary Examiner*—Christopher Kilner
*Attorney, Agent, or Firm*—Oliff & Berridge

[57] ABSTRACT

An organ storage device permits both static storage and perfusion of an organ without removing the organ from an organ container. The organ storage device includes a contoured organ container. The organ container is stored and transported in an insulated temperature controlled static storage module. The container module is equipped with monitoring devices for monitoring the organ during storage and transportation. The container module is also equipped with an assembly for connecting the organ container to a perfusion module.

21 Claims, 6 Drawing Sheets

PORTABLE DEVICE FOR PRESERVING ORGANS BY STATIC STORAGE OR PERFUSION

BACKGROUND OF THE INVENTION

This invention relates to apparatus for the storage of organs for transplantation and physiology in general and, more particularly, to apparatus for the storage of an organ securely held and maintained at a desired temperature during either static storage or perfusion of the organ.

As improvements in clinical transplantation of human organs advance, there is a growing need for preserving organs until they can be transplanted. Because the location of the donated organ may be a considerable distance from the transplantation location and there may be delays prior to transplantation, it is necessary to preserve the organ while transporting the organ to the place of transplant or holding the organ at the place of transplant.

Currently, organs preserved for clinical transplantation are stored either by being placed into a container and surrounded by ice or by being continuously perfused. Continuous perfusion provides superior storage of organs but is rarely employed because of the expense, hazardousness, and awkwardness of transportation as compared to the overall convenience and inexpensiveness of ice storage.

The static storage of organs in ice has a number of disadvantages that have not received adequate attention to date. For example, organs stored in conventional plastic containers may be harmed during transport by unrestrained or insufficiently restrained movements within these containers. The shapes of these containers bear no resemblance to the shapes of the organs contained therein. This may result in the collision of the organ with the walls of the container causing damage to the organ.

Some surgeons have recognized this and provide some protection against collision by placing gauze pads surrounding the organ. This practice may also damage the organ. Gauze may contain or shed particulates into the perfusate or fluid that may become emboli if introduced by chance into the artery. Additionally, gauze, by design, has a somewhat rough surface. Kidneys and hearts may be physically solid enough to resist damage from contact with this rough surface. Livers, pancreases, and lungs, however, are remarkably delicate and may be harmed by contact with gauze. The use of cloth towels may also be ineffective due to uneven organ support or insufficient space for towels in the container.

The storage of the organ in an ice chest also exposes the organ to possibly harmful vibrations. The vibrations encountered by the ice chest are transferred to the organ within the container (such as, for example, shocks from rolling a cart holding the chest over a tile floor or a sidewalk, slamming the ice chest down onto a receiving surface, rolling the cart off a sidewalk and onto a street, transporting the chest over railroad tracks or sitting on the seat of a vibrating small aircraft). These vibrations or shocks may, again, damage the organ. The same vibrations may also damage an organ subjected to standard continuous perfusion.

Recent research indicates a general tendency toward cold denaturation of many proteins at 0° C. and empirical observations on the storage of organs at temperatures above 0° C. indicate that the storage of organs above 0° C. is superior to storage at 0° C. This is applicable for static organ storage. This implies that the use of ice does not provide for organ storage at an optimum temperature. To the contrary, the storage of organs in ice may actually result in damage to the organ. It is entirely possible that the detrimental effects of long-term ice storage are due primarily to cold denaturation and/or storage at a suboptimum temperature.

A further disadvantage of the use of ice for storing organs is that ice melts. This melting limits the available storage time and also raises the need to dispose of the melted ice or to find new ice during transportation of the organ. Furthermore, it also requires that an ample supply of ice be on hand at the originating hospital.

Additionally, ice is generally not sterile. The storage of organ containers surrounded by ice raises a genuine hazard of contamination of the organ. Microbes from the melted ice that covers the lid of the storage container may contaminate the organ when it is removed from the storage container. The microbes may then be transplanted into the immunosuppressed recipient. It may be very difficult to avoid this problem.

Furthermore, the viability of an organ stored in a container in ice cannot be judged. Additionally, the storage history of the organ cannot be verified. Typically, organ temperature cannot be checked after transport to ensure the absence of any irregularities. Also, the actual, verifiable cold storage time, which may be critical for evaluating the suitability of an organ, may not be known or may not be known with sufficient accuracy.

An apparatus for perfusing organs at a reduced cost, reduced risk, and with fewer transportation difficulties and that would allow the detrimental effects of prolonged ice storage to be avoided is desirable. There have been recent attempts to provide portable perfusion apparatus for transporting organs. None of these perfusion machines protect the organ from the eventuality of damage due to uncontrolled warming if the perfusion machine should stop functioning for any reason.

U.S. Pat. No. 3,995,444 to Clark et al. discloses a portable organ perfusion system. The system provides for extracorporeal perfusion of organs wherein a pulsatile flow of cold perfusate is circulated through an organ intended for transplantation. The system includes a perfusion chamber, a heat exchanger comprising ice water bath containing a coil of tubing through which the perfusate is circulated, and a pulsatile pump interposed in the line between the heat exchanger and the perfusion chamber, downstream of that exchanger, for drawing cold perfusate through the exchanger and directing it in a series of regular pulses to the organ.

U.S. Pat. No. 4,745,759 to Bauer et al. discloses a portable machine that may be operated by a portable battery pack. The machine is capable of perfusing one or more organs in a temperature controlled environment. A thermoelectric refrigeration system regulates the temperature of the perfusate delivered to the organ. The temperature of the perfusate is automatically controlled within selectable parameters by microprocessor circuitry. An alarm system calls attention to changes in temperature, pressure, flow and voltage parameters that exceed selected conditions. The Bauer perfusion system and the perfusion systems produced by Waters Instruments of Rochester, Minnesota do not include any thermal insulation for the organ cassette.

U.S. Pat. No. 5,217,860 to Fahy et al. discloses a computer-controlled apparatus for perfusing an organ. The apparatus includes a plurality of fluid reservoirs and an organ container. One or more sensors are located within the fluid flow path for sensing the concentration, temperature, pH and pressure of the fluid flowing through the apparatus. The apparatus is contained within a refrigerated cabinet.

The present invention provides a novel approach to organ perfusion which precludes rapid organ warming when perfusion is terminated, and is designed also to function as a static storage device for organs.

SUMMARY OF THE INVENTION

The invention provides an improved device for the storing and transporting of organs. The storage device eliminates disadvantages of ice storage and disadvantages of continuous perfusional preservation. This is accomplished by combining perfusion with static storage, in part by a fundamentally new approach to organ "packaging" and temperature control, and in part by instrumenting and/or computerizing both perfusion and static storage so that pertinent data can be readily and objectively documented and retrieved on demand and so that storage and perfusion conditions can be properly controlled.

The storage device includes an organ container having interior contoured pads for receiving an organ. The organ container is located within a temperature controlled storage box that is capable of being converted from a static storage state to a perfusion state. A perfusion module can be added to or removed from the organ static storage module at any time to allow conversion from static storage to perfusion and back again as desired, and all without loss of documentation of the organ's preservation history. The device contains built-in sensors and an interface to a built-in microprocessor as well as a keypad and a display for entering and retrieving information.

BRIEF DESCRIPTION OF THE DRAWINGS

This invention will be described in detail with reference to the following drawings in which like reference numerals refer to like elements and wherein.

DETAILED DESCRIPTION OF PREFERRED EMBODIMENTS

Figure 1:
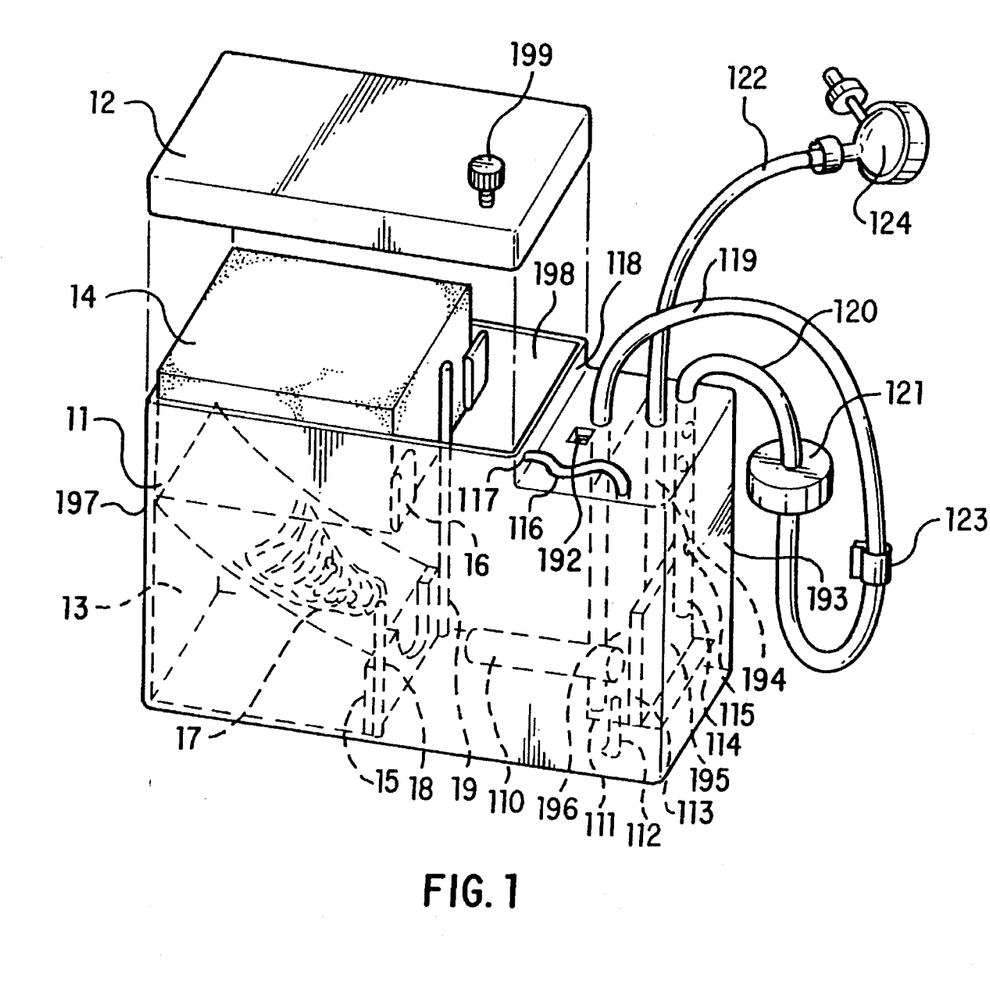
FIG. 1 is a schematic depicting a contoured organ container according to the present invention.

FIG. 1 depicts an organ container according to an embodiment of the invention. The organ container 11 is formed of a thin sturdy molded plastic. The container 11 may be transparent to permit viewing of the contents of the container without removing lid 12. The lid 12 may be snapped on to the container 12. It is sufficient to maintain sterility of the contents of organ container 11. The lid 12 contains a captured screw plug 199. The screw plug 199 may be used to vent the container 12 at the beginning of organ perfusion when perfusion is first selected.

The container 12 includes a pad 13 for receiving an organ. The pad 13 consists of a soft sterile foam material. This foam material may be similar to the soft foam inserts normally used to package non-living materials for shipment. Pad 13 is sufficiently soft such that it conforms to the contour of the organ transported thereon. The pad 13, however, is sufficiently firm to support the weight of the organ and to prevent lateral motion of the organ on the pad. Pad 13 is tapered having a taller section adjacent a back wall 197 of the container 11. The center of the pad 13 contains a depression 17 for cradling the organ. Alternatively, pad 13 may be inflatable and the depression 17 in pad 13 for cradling the organ may be formed largely during inflation of the pad.

The container 11 also includes pad 14. Pad 14 is positioned in the container 11 after the organ is positioned on depression 17 in pad 13. The pad 14 is pressed down on to the organ when the lid 12 is placed on the container 11. Pad 14 may have generally the same construction as pad 13. Pad 14 also shapes itself to the dimensions of the particular organ being transported. Pad 14 also prevents lateral and vertical movement of the organ within the container. Alternatively, pad 14 may also be inflatable.

Pads 13 and 14 carry out functions that are analogous to the much firmer styrofoam pads used for the shipment of objects such as computers, for example, which need be supported only at key positions. This approach permits sufficient flexibility to accommodate any size or shape of organ without sacrificing adequate restraint of organ motion. The pads 13 and 14 provide better support and protection of the organ within the container than gauze or even surgical towels. Additionally, the foam pads 13 and 14 are less likely to introduce particulates into the container. Therefore, the likelihood of contaminating the organ is reduced. The pads 13 and 14 may be coated with a thin highly flexible sterilizable plastic layer to further impede the introduction of particulates and improve sterilizability.

Pad 13 is tapered toward the center of the container 11. In addition to preventing motion of the organ, this arrangement tilts the organ so as to direct arterial and/or venous vessel(s) of the organ (including the portal vein in the case of the liver) toward a perfusion tube 110 located near the bottom of container 11. Barrier 15 is provided in the container 11 to support the pad 13 within container 11 to prevent motion of the pad 13 toward the center of the container 11. Barrier 15 contains a central depression, as shown in FIG. 1, to permit easy passage of organ vessel(s) toward the perfusion tube 110. A pair of barriers 16 positioned on either side of container 11 act to restrain the movement of pad 14 toward the center of the pad 14. Each barrier 16 is constructed so as to adequately retain pad 14 in position without unduly interfering with placement of the organ into container 11. Pad 14 is further immobilized by contact between it and the organ below and the lid 12 above. The side of pad 14 in contact with barriers 16 may be reinforced to prevent pad collapse at its contact points with barriers 16.

The organ container 11 includes a perfusion tube 110. The perfusion tube 110 is generally constructed of a plastic material such as, for example, a heavy-walled Silastic® tubing. Tygon® and a variety of other flexible, medical-grade plastics are acceptable alternatives to Silastic®. This permits a firm grip of tube 110 on the organ's cannula (previously inserted into the organ's vessel by the surgeon at the time of organ removal from the donor) while permitting sufficient flexibility of tube 110 to enable easy insertion of the cannula into the tube 110.

Alternatively, perfusion tube 110 can readily be converted to a U-shaped terminus, not shown, using an adaptor or using a version of the container that is specifically constructed for use with organs that have double inputs (such as the liver, which may use both the portal vein and the hepatic artery for arterial perfusion, or kidneys with double renal arteries).

The organ container 11 and the perfusion tube 110 are constructed such that the surgeon can easily locate the organ within the container and engage the cannula with the perfusion tube 110. The arrangement of the pad 13 within the container 11 permits the cannula to easily reach perfusion tube 110. The cannula can be easily inserted into tube 110 and requires no external ligation or other compression of tube 110 to secure the cannula(e) in place. The opening 198 in the container 11 is considerably longer than the distance between the back wall 197 of the container and barriers 15 and 16, and is sufficiently long to fully expose the open end of perfusion tube 110 to view from directly above. This extended length of opening 198 facilitates connection of the organ cannula(e) with perfusion tube 110 and subsequent disconnection.

Perfusion tube 110 extends from a bubble trap 111. Bubble trap 111 is comprised of two compartments, a rear compartment 196 from which tube 110 extends, and a forward compartment 195 into which an arterial line 114 empties. The forward and rear compartments 195 and 196 are separated by a partition 113. The partition has a height that is sufficiently low to provide adequate flow of perfusate from the forward compartment 195 to the rear compartment 196 so as to avoid the danger of introducing air into the organ. Air introduction might occur when the volumes of the fluid in both compartment 195 is sufficient to surmount the height of partition 113. The partition 113 also is sufficiently high to ensure that the end of fluid delivery line 114 is below the top of partition 113. This second constraint on the height of partition 113 derives from the fact that the purpose of partition 113 is to ensure that bubble trap 111 fulfills its purpose of preventing bubbles from entering the organ through perfusion tube 110. More particularly, partition 113 ensures that any bubbles or air that may enter bubble trap 111 from input line 114 are directed upwards toward the top of bubble trap 111 rather than being allowed to be carried downward toward tube 110.

Similarly, input line 114 may optionally be perforated near the top of trap 111 with holes 115. These holes 115 will permit air to escape from tube 114 and rise to the top of bubble trap 111 before reaching the bottom of tube 114 should air be present in the fluid entering tube 114. Additionally, this will permit fluid to escape from the tube in several places rather than only at the bottom of tube 114. This will reduce the turbulent flow of the perfusate, thus reducing the chance of creating bubbles. Tube 114 is necessary because without it, perfusate coming into the bubble trap would impact on the surface of the liquid within the trap, thus creating small bubbles which might be drawn into tube 110. In normal operation, perfusate coming into the trap from tube 114 should be essentially devoid of air, so the absence of tube 114 would increase a risk of air embolization.

Organ container 11 contains invaginations 18, 19, and 112. These invaginations are thermal wells intended for the insertion of metal-sheathed thermocouples (or thermistors) from below. These sensors are mounted in the floor of the cavity into which the organ container 11 is placed. Thermal well 18 permits temperature sensing near the level of the midline of the organ. Thermal well 18 has a height sufficiently short to avoid interfering with cannula insertion into tube 110 and to avoid direct and potentially physically damaging contact with the organ.

Thermal well 19 permits temperature sensing near the top of container 11 and the top of the organ. Thermal well 19 is located sufficiently close to a wall of container 11 such that it does not present an obstacle to the introduction of the organ cannula(e) into perfusion tube 110 by the surgeon. Also, the thermal well 19 is positioned a distance from the wall of container 11 to sample, as much as possible, the temperature of the top of the container rather than of the side of the container because the latter is expected to be better controlled than the former.

The thermal well 112 permits temperature sensing inside the rear compartment 196 of bubble trap 111. The thermal well 112 is positioned to sample the temperature of the perfusate fluid near its entry point into perfusion tube 110. The thermal well 112 extends upward through the floor of bubble trap 111. An acceptable alternative to termination of well 112 within the fluid compartment of trap 111 is termination within the wall of trap 111 from which tube 110 originates. This alternative, while not preferred, may be elected should it permit significantly easier manufacturing of the apparatus (avoidance of any difficulties with leakage of rear compartment 196 into the main cavity of container 11). In the event this alternative is selected, the well 112 should be located as near as possible to the fluid of the rear compartment 196.

A vent line 116 is located on top of the bubble trap 111. This permits venting of the bubble trap 111 as container 11 is filled with a pre-cooled solution such as, for example, Viaspan® (also known as University of Wisconsin or UW Solution). Viaspan® not only preserves organs very well, but it is often suitable for both static organ storage and for perfusion. In cases in which it is not suitable for both static organ storage and for perfusion, a more suitable solution may be substituted. During the operation of filling the container 11 with pre-cooled solution, the bubble trap 111 will not be filled unless it is vented. Because the top 194 of bubble trap 111 is located vertically below the opening 198 of organ container 11, vent line 116 has the capacity of allowing almost complete filling of bubble trap 111 with pre-cooled solution. The difference in height between opening 198 and trap top 194 also allows vent line 116 to enter the wall 118 at site 117. This arrangement permits the closure of the vent line 116 when the bubble trap 111 has been filled. When the lid 12 is pressed into place on container 11 and forms a seal, the lid 12 will occlude vent line 116 at site 117, thus closing it firmly and eliminating its venting function. This method of closure of vent line 116 is preferred to the use of a manual clamp. It requires no thought on the part of the user. Venting is terminated as soon as lid 12 is placed on container 11.

Line 119 is a venous line by which fluid is withdrawn from organ container 11. The open end of line 119 is located near the bottom of container 11. This ensures withdrawal of fluid rather than of air from container 11 and further ensures sampling of fluid that is in good thermal contact with the cooling material surrounding the organ container 11 as described below.

Figure 2:
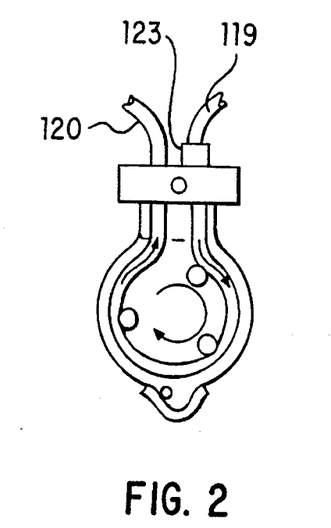
FIG. 2 is a schematic view of a creep limiter for the organ perfusion tubing according to the present invention.

The venous line 119 is contiguous with arterial line 120. The arterial line 120 is connected to line 114 and is located outside of the bubble trap 111. A creep limiter 123 allows the tubes 119 and 120 to be inserted into the head of a roller pump to permit fluid withdrawal from organ container 11 via tube 119 and return to organ container 11 via tube 120 without creeping of tubes 119 and 120 through the roller pump head, as shown in FIG. 2.

One or both of the lines 119 or 120 may include a port, not shown, at a site that would be accessible during organ perfusion to permit fluid samples to be taken for later analysis or that would permit drugs to be injected to stabilize the organ. Such a port would be entered by passing a sterile needle through a diaphragm in a standard Luer closure and withdrawing the sample into or ejecting it from a sterile syringe.

The arterial line 120 includes a filter assembly 121. The filter assembly 121 is essential for removing particulates such as fat particles or blood clots that may be introduced into container 11 along with the organ. Although not considered essential, it is considered very desirable for this filter to continuously filter and sterilize the perfusate to guard against any inadvertent introduction of microorganisms in any manner into container 11.

Organs can be perfused at low temperatures through a single sterilizing filter for at least 18–24 hours with volumes of as much as 21 liters of viscous, polymer-rich perfusate without serious loading (blockage) of the sterilizing filter provided that coarser filters are placed in the fluid stream immediately before the sterilizing filter. This may be accomplished by layering three filters (e.g., a coarse particle filter, 1.2 micron filter and 0.22 micron filter) on top of each other separated by mesh spacers. Although the prior art has disclosed comparable filters, organ perfusion devices described to date, with the exception of that described by U.S. Pat. No. 5,217,860 to Fahy et al. and by Fahy (Biomed. Instru. Technol. 28: 87–100, 1994), whose function is entirely different from the function of the present invention, have not included sterilizing filters.

The organ container 11 is also provided with line 122 that leads to a pressure dome 124. Line 122 originates in the bubble trap 111 to permit arterial pressure to be determined. Line 122 does not extend below the lid of bubble trap 111 to minimize the amount of perfusate, as opposed to air, that enters line 122 when pressure is generated within the bubble trap. The pressure dome 124 may include a second arm, as shown in FIG. 1, for connection to a mechanical pressure gauge (e.g., a sphygmomanometer gauge) to permit manual checking of perfusion pressure and calibration of the microprocessor controlled pressure sensing. A stopcock may be provided in line 122 should, due to operator error, the organ be perfused without connecting dome 124 to its mating sensor, resulting in damage to and leakage from dome 124.

The container 11 is also provided with a sensor port 192. The sensor port 192 is designed to admit a specially-designed sterile pH electrode or other sensor which is screwed into a sterile, sealed position through port 192.

It should be noted that the bubble trap 111 is deliberately constructed to have a relatively large volume. This is due in part to the impossibility of fully priming lines 119 and 120 and filter assembly 121 before use without introducing air into bubble trap 111. For this reason, bubble trap 111 must be large enough to readily accommodate the air that will occupy the lines 119 and 120 and the filter assembly 121 prior to their use for the first time. After this initial use, no further air should enter bubble trap 111, but the trap is large enough to impose a safe distance between the air at the top of the trap and tube 110. If priming is considered highly desirable, it can be achieved by activating the perfusion pump manually prior to organ insertion into container 11 with lid 12 ajar.

Figure 3:
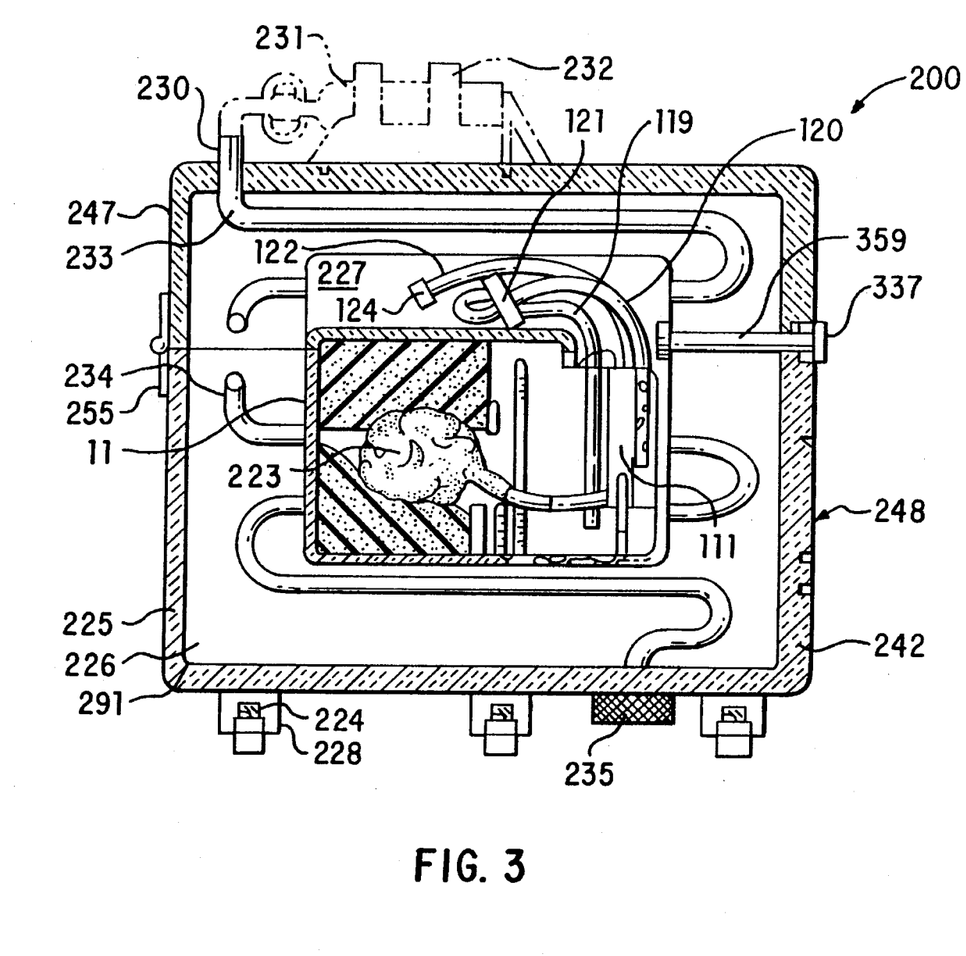
FIG. 3 is a cross-sectional side view depicting the contoured organ container of FIG. 1 in a static storage module according to the present invention.

The inability to prime lines 119 and 120 and filter assembly 121 prior to their use without making a specific effort to do so is a result of locating them at the top 194 of trap 111. This configuration, however, is chosen to permit close apposition of the wall 193, and of the lateral walls of organ container 11, with the walls of the cavity 227 in which the organ container 11 resides, as shown in FIG. 3. This is desirable not only for better thermal coupling between organ container 11 and its environment, but also to reduce dead spaces that contribute to the overall dimensions of the complete device, which is desired to remain as small as possible.

The operation of the organ container 11 will now be described. Initially, the container 11 is filled with the pre-cooled solution, discussed above. The container 11 may then be transferred to an ice environment for maintenance of low temperatures while the organ is being prepared for transfer to the container 11. In this step, the lid 12 of the container is not exposed to ice in order to remove the danger of contamination. The step involving icing the organ container can be eliminated when it is not awkward or hazardous for the surgeon to put the organ into the organ container while the organ container is pre-seated in its permanent environment. During the holding time prior to accepting the organ, the bubble trap 111 will self-prime. The organ is then placed onto the pad 13 within the container. The arterial vessel(s) extending from the organ will then be joined to perfusion tube 110, as described above. The container 11 may then be filled with additional pre-cooled solution to replace any solution that has migrated into the bubble trap, if the volume of the organ is less than the volume of the bubble trap. The pad 14 is then applied and the lid 12 snapped shut over the organ, sealing tube 116 and hermetically sealing the entire system. The tubes 119 and 120 and the filter assembly 121 are then placed on the lid 12. The container 11 is then transferred to an organ shipping box 200, where the thermocouples for wells 18, 19, and 112 automatically slide into the wells without any effort on the part of the user due to the alignment of the organ container 11 with the walls of the storage box 200. The box 200 is then closed for long-term storage and/or transport of the organ.

The organ container 11 as described may be used exclusively for static storage. The organ container 11 can be simplified when the clinical intention is exclusive use of static storage without the possibility of perfusion. This simplification is desirable to avoid unnecessary costs for the user. In such an arrangement, perfusion tube 110, bubble trap 111, invagination 112, partition 113, arterial line 114, holes 115, vent line 116, site 117, venous line 119, arterial line 120, filter assembly 121, line 122, creep limiter 123, pressure dome 124, top 194 of bubble trap 111, forward compartment 195, rear compartment 196 and screw plug 199 may be eliminated. With such an arrangement, the walls 118 and 193 become contiguous (i.e., a single wall similar to wall 197).

An organ shipping box 200 for the organ container 11 will be discussed with reference to FIGS. 3–5. The organ shipping box 200 includes two main parts, a lid 247 and a base 248. The lid 247 and the base 248 are preferably connected on one side by at least one hinge 255. Each hinge 255 must be of high quality and sturdiness to permit precision closing of the lid 247. At least one latch 254, shown in FIG. 5, is provided to maintain the lid 247 and base 248 in a closed position. A connecting tube 249, shown in FIG. 5, conveys gaseous coolant within the cooling system 233 and 234 in lid 247 and base 248. The connecting tube 249 may be flexible or detachable to permit opening of the lid 247. The shipping box 200 rests on legs 228 that contain shock absorbers 229 for dampening vibrations that may be transmitted to the organ with damaging effects. The base 248 and the lid 247 form a cavity 227, shown in FIG. 3, that contains the organ container 11 including lines 119 and 120, the filter assembly 121 as well as pressure line 122 and terminal cap 124. The lid 247 and the base 248 each include a cooling material 226, an external insulation 225, and a cooling system 233 and 234. The cooling material 226 is contained in a tank 291.

The cooling material 226 is a material having a melting point equal to a desired storage temperature of the organ. This melting point may vary from organ to organ depending upon the ideal storage temperature for a particular organ. Although the different desired organ-specific storage temperatures are not known with precision at this time, the range of expected temperatures that encompass all possible temperature optima is believed to be 0° C. to 15° C. for static storage and 3° C. to 30° C. for perfusion with the greatest emphasis being placed on the temperature region from about 3° C. to 13° C. overall.

Most organs are continuously perfused at about 8° C. to 10° C., and the optimal temperature for static storage appears to be within the range of about 4° to 10° C. Thus, the temperature range that is currently most likely to be valuable for both static storage and continuous perfusion is 6°±2° C. Preferred materials for use as cooling materials in this temperature range (4° to 8° C.) are specified in Table 1. Viable but currently less preferred candidates are specified in Table 2. Also, the cooling material 226 is not merely limited to a pure substance but may be a eutectic. The criteria for selecting a cooling material include a melting point in the desired range; relatively low toxicity, explosion or vaporization hazard, flammability, and corrosiveness; relatively good packageability; chemical stability; affordability; and a relatively high latent heat of fusion (i.e., number of calories required for melting the frozen material per gram or per milliliter). Additionally, a relatively small volume change upon freezing and melting is preferred to avoid stressing tank 291 or creating a need for inclusion of air in tank 291 to permit expansion and contraction of the cooling material.

Despite the latter concern, tank 291 may nevertheless be filled successfully with pure water so that cooling material 226 is ordinary ice. If essential, ice-free compartments can be included in the cooling material region to eliminate expansion-related damage to the tank 291 and the surrounding insulation.

Ice is a very effective thermal buffer per unit volume, per unit weight, and per dollar and is expected to be strongly favored whenever storage at 0° C. for the time required is not seriously more detrimental than storage at higher temperatures. Cooling material 226 may be any substance of any kind that is suitable for the conditions of use desired. Should mechanical refrigeration be employed, cooling material 226 can even be a liquid over the full range of temperatures of interest. Further, the design described does not preclude introducing more than one individually packaged coolant into one organ shipping box coolant compartment.

TABLE 1**

| Storage Temperature (°C.) | Preferred Thermal Buffers (Melting point), d = density |
|---|---|
| 4–5 | Heavy water ($D_2O$) (3.82° C.), 76 cal/ml, d = 1.1 |
| | Glycerol triacetate (4.1° C.), d = 1.16 |
| | Selenium oxyfluoride (4.6° C.), d = 2.67 |
| | 1,3-butanediol sulfite (5° C.), d = 1.24 |
| 5–6 | 2,5-dichlorotoluene (5° C.), d = 1.25 |
| | o-Acetylphenol (5 ± 1° C.), d = 1.13 |
| | Silicon Tetrabromide (5.4° C.), d = 2.77 |
| | Dibromodinitromethane (5.5° C.), d = 2.44 |
| | Benzene (5.5° C.), 26.8 cal/ml, d = 0.88 |
| | 3,3-dimethylbutanol (5.6° C.), d = 0.81 |
| | 2-bromophenol (5.6° C.), d = 1.49 |
| | 2,5-dibromotoluene (5.6° C.), d = 1.81 |
| | Nitrobenzene (5.7° C.), 27 cal/ml, d = 1.20 |
| | 1,4-diiodobutane (5.8° C.), d = 2.35 |
| | Salicylisobutyl ester (5.9° C.), d = 1.06 |
| 6–7 | Boron fluoride dihydrate (6° C.), d = 1.63 |
| | Diiodomethane (6.1° C.), d = 3.33 |
| | 2-methoxyaniline (6.2° C.), d = 1.09 |
| | 3,3-dimethyl butanoic acid (6.5 ± 5° C.), d = .91 |
| | 2-methylcyclohexanol (7° C.), d = .94 |
| 7–8 | 4-amino-3-chlorotoluene (7° C.), d = 1.15 |
| | 4-chloro-3-nitrotoluene (7° C.) |
| | 1,2-dibromobenzene (7.1° C.), d = 1.98 |
| | Methylmaleic anhydride (7–8° C.), d = 1.24 |
| | 4-methoxy ethylbenzoate (7–8° C.), d = 1.10 |
| | 4-chlorotoluene (7.5° C.), d = 1.07 |
| | (d,l)-2,3-butanediol (7.6° C.), d = 1.00 |
| | (dl)-succinic acid ethyl ester (8° C.), d = 1.15 |
| | Octylphenyl ester (8° C.), d = 0.91 |
| 8–9 (cursory listing) | Tribromomethane (8.3° C.), d = 2.89 |
| | Formic acid (8.3–8.4° C.), 80.6 cal/ml, d = 1.22 |
| | Betel phenol (8.5° C.), d = 1.06 |
| | 4-pyridine carboxylic acid method ester (8.5° C.), d = 1.16 |
| 9–10 (cursory listing) | m-bromoiodobenzene (9.3° C.), 23.2 cal/ml, d = 2.26 |
| | 1,2-dibromoethane (9.8–9.9° C.), 30.1 cal/ml, d = 2.18 |

**Source of melting point and density data: Handbook of Chemistry and Physics, 56th Edition (1975–1976), Robt. C. Weast, Editor. CRC Press, Cleveland.

TABLE 2*

| Storage Temperature (°C.) | Some Viable but Less Immediate Candidates (Melting Point), d = density |
|---|---|
| 4–5 | 1-bromo-4-ethoxybenzene (4° C.), d = 1.41 |
| | 5-methoxysalicylaldehyde (4° C.), d = ? |
| | 2-bromodecanoic acid (4° C.), d = 1.19 |
| | 1-iodonaphthalene (4.2° C.), d = 1.74 |
| | 5,8-dimethylquinoline (4–5° C.), d = 1.07 |
| | 1-phenyl-(trans)-1,3-butadiene (4.5° C.), d = .93 |
| | Chlorotrinitromethane (4.5°), d = 1.68 |
| | 3-methylbiphenyl (4.5° C.), d = 1.02 |
| 5–6 | Methyl-laurate (5.2° C.?), d = 0.87 |
| | 2-mercaptophenol (5–6° C.), d = 1.24 |
| | 1-ethoxynaphthalene (5.5° C.), d = 1.06 |
| | Diethyl suberate (5.9° C.), d = 0.98 |
| | 3-chloro-2-hydroxy biphenyl (6° C.), d = 1.24 |
| 6–7 | Tridecylbromide (6.2° C.), d = 1.018 |
| | Tridecanoic acid methyl ester (6.5° C.), d = ? |
| | (trans)-Isosafrole (6.8° C.), d = 1.12 |
| 7–8 | 1-decanol (7° C.), d = 0.83 |
| | 3-bromo-propoxy benzene (7–8° C.), d = 1.365 |
| | Pentylcyclohexane (7–8° C.), d = 0.95 |
| | 1,4-dimethylnaphthalene (7.66° C.), d = 1.02 |
| | Carbonic acid bis-(2-chloroethyl) ester (8° C.), d = 1.35 |

TABLE 2*-continued

| Storage Temperature (°C.) | Some Viable but Less Immediate Candidates (Melting Point), d = density |
|---|---|
| 8–10 | 1-tetralone (8° C.), d = 1.10<br>1,1-dichloro-2-methyl-2-propanol (8° C.), d = 1.24<br>3,5-dimethyl benzaldehyde (9° C.), d = ?<br>Anabasine (9° C.), d = 1.046<br>Chlorostannic acid ($H_2SnCl_6$).6($H_2O$) (9°, d = 1.93)<br>Selenium oxychloride ($SeOCl_2$) (8.5–9.8° C.), d = 2.42<br>Iodine hexafluoride (9.6° C.), d = 3.75 |

*Source as in Table 1

The cooling system 233 and 234 may be a standard refrigeration system, but a more novel concept is depicted in FIG. 3. In a preferred embodiment of the present invention, cooling is created by allowing compressed gas to expand. The gas is passed through a network of tubing that extends through the base 248 and lid 247. The cooling associated with expansion of $CO_2$ gas, for example, can drive temperatures as low as −79° C. (the freezing point of carbon dioxide). Given that temperatures this low are not necessary (and may even be undesirable), cooling by gas expansion should be adequate. Given that $CO_2$, $N_2$, and even $O_2$ may create undesirable effects after release to a confined space such as an airplane atmosphere (including asphyxiation, narcosis, acidosis, oxygen toxicity, or an explosion hazard), the ideal gas of choice and the cheapest possible choice is compressed air.

By using compressed air to create cooling of the cooling material, several highly desirable objectives are achieved. A power source is unnecessary to maintain the desired temperature. As a result, no lengthy recharging time is necessary, unlike the situation for a battery. "Recharging" consists of simply replacing the tank with a new tank, a process that will require 1–2 minutes rather than several hours. Although battery power may be required for functions other than cooling (e.g., for powering a microprocessor), the use of compressed gas expansion cooling rather than battery-powered cooling conserves battery power for those non-cooling functions.

The use of compressed air allows cooling to be accomplished in any environment, at any time. When temperature begins to drift upward, a valve on the air tank is simply opened for a specified period of time and then closed. The temperature will then return to the desired value (and should not fall by more than about 1° C. as most of the cooling material mass freezes). Unlike compressor-driven refrigeration, there are no mechanical parts to fail. The cooling system cannot malfunction. No servicing is needed.

Also, cooling with the expansion of compressed air is immediate, whereas cooling by compressor is slow. Standard refrigeration is based on gas expansion within a closed system in which gas escape must be prevented. Little gas can be contained in a refrigeration system, and thus little expansion can occur at any given time. The expansion of gas from a compressed air cylinder, on the other hand, is not so limited. Gas expansion from a tank will allow re-freezing of the cooling material to be achieved in minutes for immediate shipment readiness or re-stabilization of the temperature. The box 200 can be maintained at room temperature in the originating hospital until organ retrieval is drawing near, at which time it can be prepared simply by opening a valve for approximately 5 to 10 minutes or so to freeze the cooling material. This minimizes the need for advance notice of organ availability and, for the medical technician performing it, the cooling is also less time-consuming (the time required is the few seconds needed to open a valve at the beginning of cooling and to close it at the end), less distracting (the med tech can remain in the operating room), and less bothersome than retrieving ice to fill an ice chest.

Furthermore, the compressed air tank 231 can be detached when not needed, and need not travel along with the shipping box if adequate thermal buffering is achieved prior to shipment or if compressed air is available at the box's destination. This allows the box 200 to attain the minimum possible weight and volume, similar to the weight and volume efficiency achieved by conventional static storage systems that do not permit the possibility of organ perfusion and do not permit recooling of the contents of the shipment box without manual replacement of melted ice. In contrast, compressors and batteries, as a general rule, must remain joined to the devices they cool.

Additionally, the compressed air can be used not only to cool but, in principle, also to pump perfusate either during or independently of cooling. Haskel pumps, for example, use only compressed air to drive fluid motions against opposing pressures of up to thousands of atmospheres. This option is not chosen as the preferred embodiment at the current time due to the relative convenience of using electrically-powered roller pumps as described below, but clearly falls within the boundaries of the current invention and may be preferred in some embodiments. Such a provision may permit the perfusion pump to be located within the organ shipping box, because the waste heat created by a pneumatically-driven pump should be much less than the waste heat generated by a conventional, electrically-powered roller pump.

The movement of expanded gas over a paddle, for example, can be used to generate electrical energy in a manner analogous to the generation of electrical energy by a hydroelectric plant or a steam-powered generator. Thus, some of the kinetic energy of the expanded gas can be captured as electrical energy as the expanded gas emerges through vent area 235 and can be used to maintain the charge on the batteries that run a microprocessor 287, shown in FIG. 5. Additionally, vent area 235, shown in FIG. 3 is intended to muffle the noise otherwise created by the expansion of the compressed air. Since the muffler 235 must act largely by reducing the kinetic energy (and hence the "noisiness") of the emerging gas, the energy capture system can also serve as this muffler. The detailed design of muffler/ energy capture system 235 is not specified as the general design and principles of such systems have already been fully described in the prior art, although never contemplated for use in this particular application.

The exhaust air from muffler/energy source 235 can be directed into an oxygenator and used to oxygenate the perfusate and to remove $CO_2$ from the perfusate if desired when the organ is being perfused.

Despite the advantages of compressed air cooling, sole reliance need not be placed on the use of compressed air as a cooling source. Compressed gas could be used as a backup to or as a booster for conventional refrigeration if desired. It is noted that the use of thermoelectric cooling disclosed in U.S. Pat. No. 4,745,759 to Bauer et al. is essentially infeasible for efficient cooling of an ice chest due to the lack of available surfaces to cool to remove the heat produced by the thermoelectric pile(s).

A tank 231 of compressed air may be located on top of the lid 247, as shown in FIG. 3. Tank 231 is attached to the organ shipping box 200 by a mounting apparatus 232, which may be any suitable apparatus (such as, for example, a bracket). Alternatively, the tank 231 can be located beneath the base 248 or strapped to the side of the base 248. The position of the tank 231 on top of the lid 247 is preferred because it is then possible for the base 248 of box 200 to rest directly on a floor. It is also desirable for the tank to be sufficiently small such that it can be transported with the box 200 should the transport conditions of the box permit the extra space and weight represented by the tank.

The tank 231 is attached to the cooling system 233 and 234 at a port 230. Ideally, port 230 is a pressure fitting. A nominally insulated tube 249, shown in FIG. 5, permits the cooling gas to pass from the lid 247 to the base 248 such that both the lid 247 and the base 248 are cooled.

FIG. 5 depicts the front of the organ shipping box 200. The base 248 includes a keyboard 250 and a data display panel 251. The display panel 251 may be tilted into a more user-friendly position 252, shown in phantom in FIG. 5. Display panel 251 may include low-energy meter displays for three internal temperature probes (T1, T2, T3), a "lid open" detector (LID), the external pressure probe (Pr) and the external pH probe (pH) as well as a computer display 288. The lid open detector (LID) would detect an open circuit caused by lid opening so that any tampering with the organ or excessive heat inleak in transit can be detected. Other features, including alarms, a display of organ flow rate and resistance, and a display of parameters such as the projected battery and tank lifetimes remaining, the temperatures of the cooling system 233 and 234 and of the cooling material 226, and a "tank present" indicator, may be included as desired. All of the elements of display panel 251 are thin such that the display panel can be built into a recess in the insulated wall together with a weather-proof protective panel.

Wires 289, running beneath or within the insulation layer 225 of base 248 and optionally of lid 247, interconnect electronic components. The display panel 251 and sensors are connected to a microprocessor 287 containing an appropriate A/D interface board as well as a D/A output capability. The microprocessor 287 and its A/D and D/A convertors are also housed in a recess in the wall of the organ shipping box.

The microprocessor 287 and its energy source should permit operation for at least 24 hours between battery recharges. Use of expanded battery packs will allow this design objective to be met. Additional operating time can be achieved by making use of the kinetic energy capturing system, described above, or even by the collection of energy by solar cells.

When the organ shipping box 200 is accompanied by a tank 231 of compressed air, it is necessary for the microprocessor 287 to be able to carry out temperature adjustment via computer actuation of the compressed gas inlet 230 via an appropriate relay. There should, however, be a manual override provision to permit human operation of the cooling system should a malfunction occur or should this be more convenient at a given time.

Figure 6:
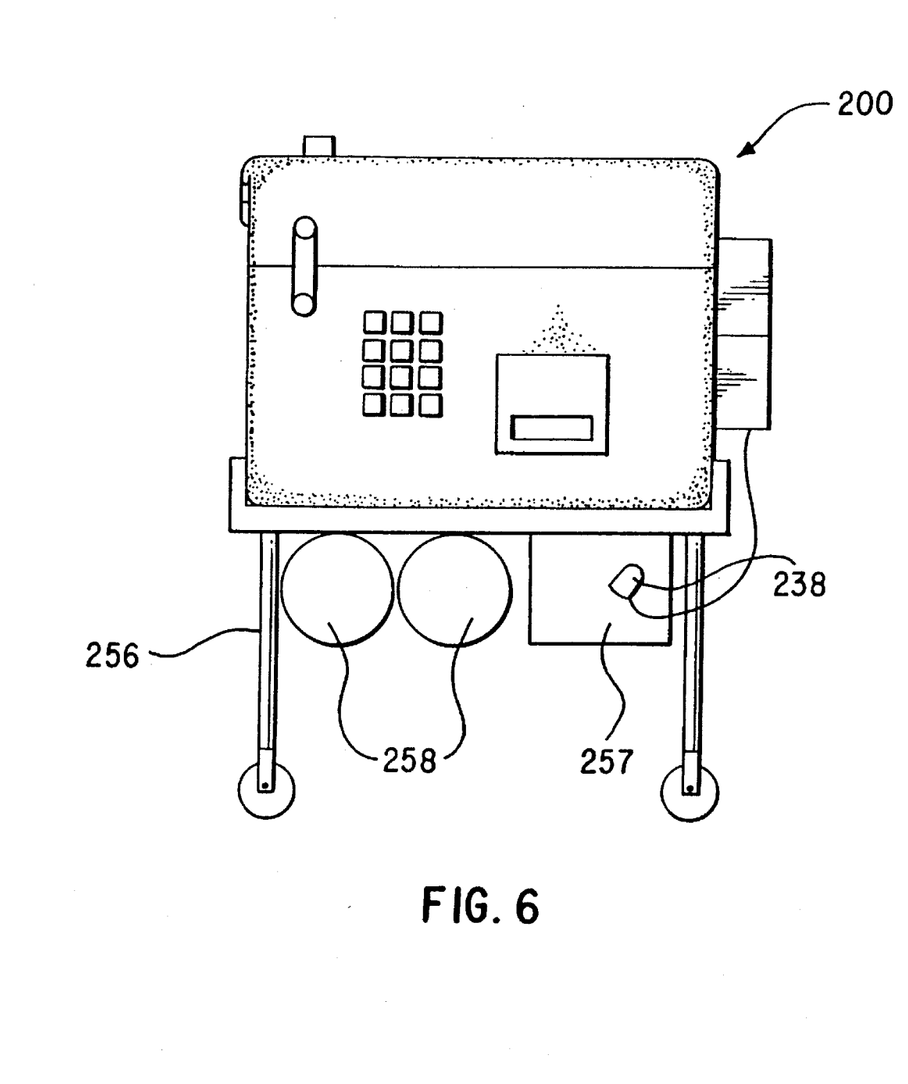
FIG. 6 is a side view depicting the static storage module positioned on the perfusion module according to the present invention.

FIG. 6 shows a preferred arrangement for long-term continuous perfusion. Generally, organ perfusion will take place either episodically, when a strong power source 257 and new compressed air tanks 258 become available, or continuously, using the benefit of a cart such as cart 256 which makes available space for the continuous presence of a powerful battery or batteries or an ordinary electrical power source (257 may be either) and backup compressed air tanks 258.

Alternatively, the perfusion cart 256 may be eliminated by using telescoping leg extensions, not shown, for legs 228 on box 200 that could be released by pressing buttons on each side of the organ storage box 200 to allow the extended legs to drop down by gravity. In such an arrangement, the tanks 258 or power source 257 may then be connected to the underside of base 248. The legs would be retractable simply by pressing the same buttons and gradually lowering box 200 to the ground.

It is contemplated that an organ may be transported to an airport using continuous perfusion as depicted in FIG. 6 and then detached from cart 256 and pump assembly 240 for transport on the aircraft, and positioned on an identical cart 256 and attached to an identical pump assembly 240 for resumption of perfusion upon arrival at the receiving airport. Once the organ shipping box 200 is positioned appropriately, as on the cart 256 of FIG. 6 or in another suitable manner, the conversion from static storage to perfusion is accomplished by carrying out the following steps, which are described with reference to FIGS. 3, 4, 7 and 8.

First (FIG. 4), a pump housing 240 having shipping box connectors 241 and 290, a pump head cover 245, a pump 239, a pressure sensor 259 and an optional sheathed sterile pH electrode with an accompanying meter (not shown) is attached to a reinforced wall 242 of the organ shipping box 200. The housing 240 may be connected by connectors 241 and 290 or other suitable fasteners such as hooks or clips. For example, the upper spur 290 of housing 240 is first inserted into a mating slot on reinforced wall 242, then housing 240 is rotated into a vertical position, bringing a hand-operated clip 241 into a docking site, where it is attached to secure the housing 240 and its accompanying devices to the box 200. The pump head cover 245 is then rotated downward to expose the pump head 246, as shown in FIG. 4. The latches 254 and organ shipping box lid 247 are then opened.

Figure 7:
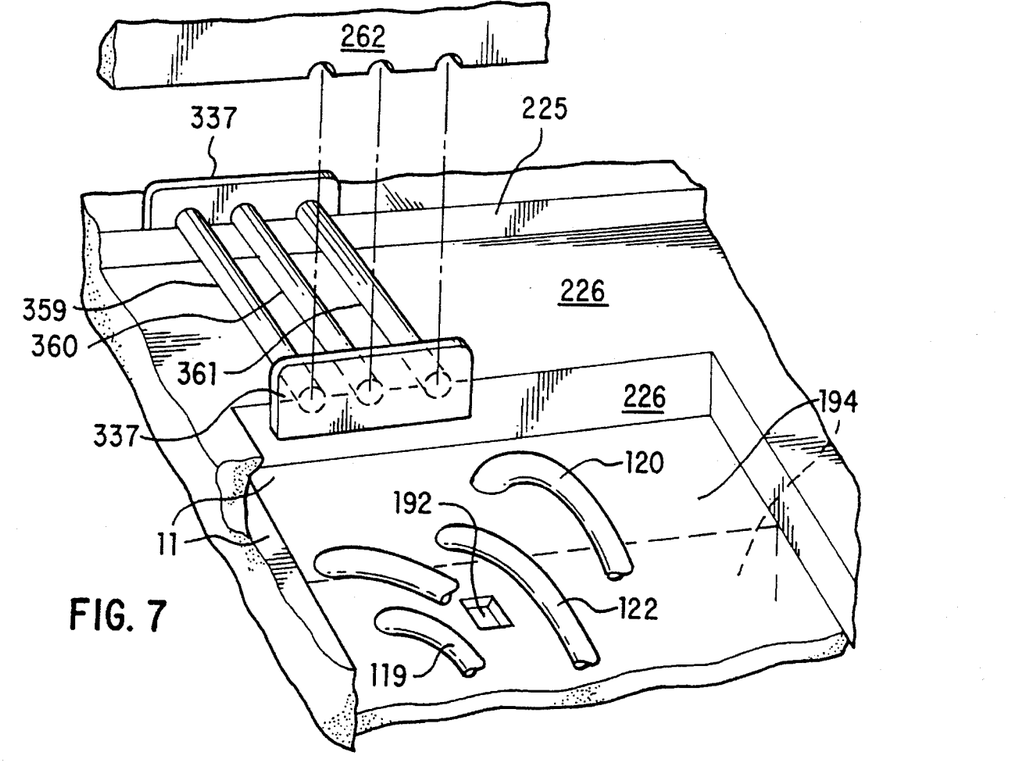
FIG. 7 depicts an insulator assembly for use in the static storage module of FIG. 3.
Figure 8:
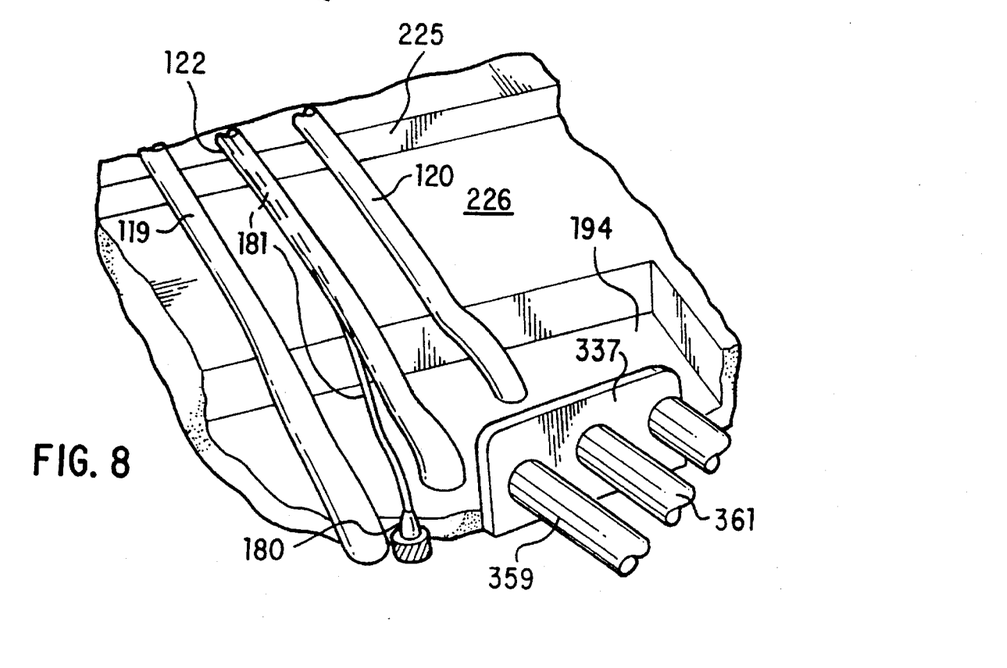
FIG. 8 depicts lines extending from the organ container through the static storage module according to an embodiment of the present invention.

The next steps are illustrated in FIGS. 7 and 8. Insulation cylinders 359–361 having controlling ends 337 are lifted out of position between the lid 247 and the base 248 and replaced by venous line 119, arterial line 120, and pressure sensing line 122, as shown in FIGS. 4, 7 and 8. Insulation cylinders 359–361 may then be placed on top of the organ container 11 in place of tubes 119, 120 and 122 and filter assembly 121, as shown in FIG. 8. FIGS. 7 and 8 depict the process for removing the insulation cylinders 359, 360, 361 and 337 from grooves in cooling tank wall 226 and 262 and in insulator layer 225 and placing venous line 119, pressure sensing line 122, arterial line 120, and the cable 181 of pH electrode 180 into these grooves.

The lines 119 and 120 are placed into the roller pump head, as shown in FIG. 2., so that slippage of lines 119 and 120 within the pump head is precluded. Other pump types may be employed such as, for example, finger pumps or pneumatic pumps.

Figure 4:
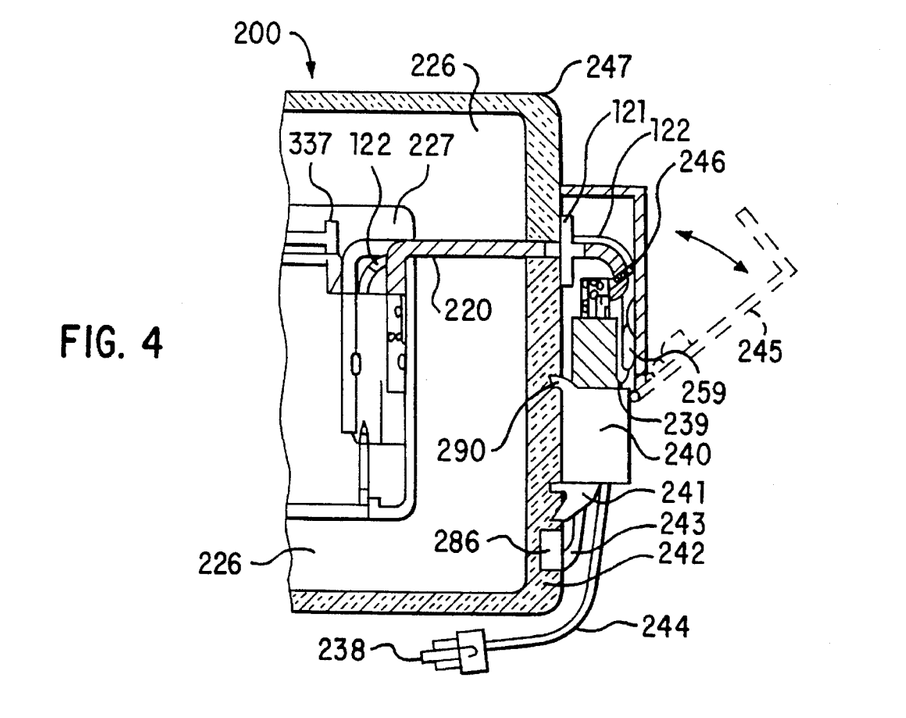
FIG. 4 is a cross-sectional side view depicting a connection between the static storage module and a perfusion module according to the present invention.
Figure 5:
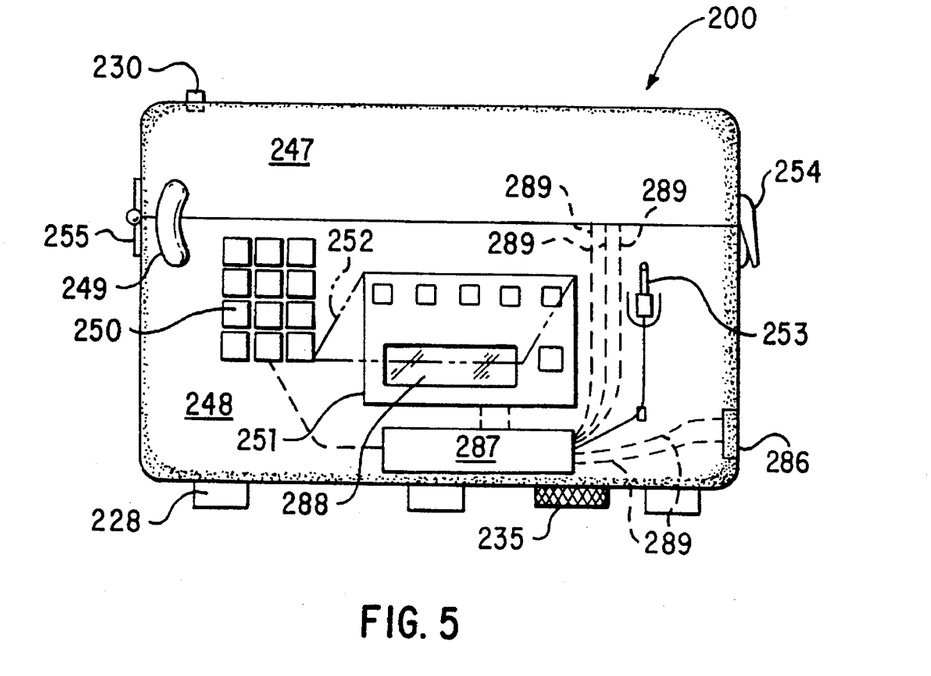
FIG. 5 is a side view of the static storage module of FIG. 3.

The pressure transducer line 122 is attached to the pressure sensor 259, as shown in FIG. 4. This may be accomplished under sterile conditions using a number of techniques. In a preferred method, a cap 124 is a standard dome for pressure sensor 259. The cap 124 is designed to snap or screw and lock onto the sensing area of sensor 259. Standard domes are separated from the sensing area of their matching transducers by thin deformable diaphragms that will not allow microorganisms to cross. Therefore, pressure can be sensed in this fashion without ever breaching the sterile environment of organ container 11.

The operator then connects the devices of assembly 240 to the organ shipping box 200 and to necessary power sources, as shown in FIG. 4. The operator plugs pump 239 into a suitable power outlet using plug 238 and connects the pressure transducer 259 to the excitation and sensing circuit of 287 by plugging cable 243 into port 286. If a pH electrode is to be used, it is extended on its pre-attached cable from assembly 240, positioned in the organ container at the site 192 of FIG. 1, and its cable tucked into the pressure transducer line groove in the wall of the organ shipping box and lid as described in FIG. 8, and its meter's cable is attached to the A/D converter through port 286. Finally, pump control jack 253, as shown in FIG. 5, is plugged into the back of pump 239 at a jack input site not shown. This entire process can be simplified by using a single plug to create all of the connections just described (with the optional exception of the plug 238), including the pump control jack connection, which would eliminate jack 253 from the front of base 248, a desirable choice. The separate connections are illustrated for the sake of clarity.

The operator then closes and latches lid 247, watching carefully to make sure precision hinge(s) 255 close the lid correctly so as to avoid damaging or occluding lines 119, 120 and 122 or the pH electrode cable. (If this hazard becomes an issue, routine modifications can be made to eliminate the hazard.) The operator tilts head cover 245 into its normal vertical position. Head cover 245 protects the components of assembly 240 from the external environment, including from ambient temperature exposure to minimize heat inleak. The arrangement shown in FIGS. 7 and 8 imposes direct contact between fluid lines 219 and 220 and the coolant tank to minimize alteration of perfusate temperature within the shipping box despite any warming that may occur during the time a given perfusate volume element is outside the box. Pump head cover 245 is ideally composed in part of thermally insulating material.

The operator presses a button on the keypad to activate the organ pump 239 and the program for controlling and recording perfusion conditions. When the operator presses a button indicating that the pump head and organ container tubing are ready for perfusion, the microprocessor automatically begins the pump 239 at a slow speed, allowing time for line priming, slow forcing of air from lines 119 and 120 into bubble trap 111, and slow delivery of fluid into the organ from bubble trap 111, permitting time for the vessels in the organ to gradually open. After priming is complete, the pump speed slowly changes as necessary to achieve the programmed target perfusion pressure (or flow). During subsequent perfusion, the pressure and flow may be held constant, may be programmed to steadily change, may be programmed to oscillate, etc. During this time, the pressures and flows actually attained, as well as all other pertinent data, are displayed and logged into permanent data storage. If desired, drug infusion can be activated using additional equipment in pump pack 240 (e.g., a syringe pump actuated by the computer) according to a desired schedule or in response to sensed conditions. Alarms may be activated when certain conditions occur, and the perfusion may be terminated by the program if conditions so warrant. Sufficient flexibility can be provided to achieve any programmed procedure desired.

To convert from perfusion to static storage, the operator presses a button on the keypad to stop the organ pump 239 and perfusion control. Lid 247 is opened. Lines 119, 120 and 122 and the filter 121 are placed in cavity 227. The thermal insulator assembly 337 and 359–361 is placed into its wall position, as shown in FIG. 7. The pH electrode is detached from port 192. The lid 247 is then closed, if appropriate, pump and sensor assembly 240 is removed.

The invention as described is capable of fully flexible operation, from static storage to perfusion. Specializations may, however, be made to achieve greater economy when less flexibility is needed, or to add even greater flexibility than shown.

If only static storage is desired, insulation cylinders 337 and 359–361 can be eliminated along with ports and wires for connection of assembly 240 devices and the specializations and wall thickening required for attachment of assembly 240 at sites 290 and 241. The microprocessor, keypad and the temperature sensors can be eliminated if data tracking is not necessary.

It is possible that the cooling material 226 could be frozen by placing the entire organ shipping box into a cold room or by filling the organ storage box with ice. Should it develop that such simple methods could suffice, the cooling system 233 and 234 could be eliminated.

The cooling material 226 might be replaceable rather than being permanently enclosed. This could be accomplished by making the top of tank 291 of the base 248, and the bottom of the tank 291 of the lid 247 removable and by packaging cooling material 226 in brick-shaped, sandbag-like packs that can be lifted or dropped out of the coolant compartment. In this case, the cooling system 233 and 234 could be structured into a vertical distribution pattern permissive of the removal and re-admission of coolant packs. Alternatively, the entire coolant compartment for both the base 248 and the lid 247 could simply be lifted or dropped out of the organ shipping box 200 as intact units and replaced by identical units containing a different type of cooling material.

The ability to change cooling material would be desirable should a different temperature be desired for perfusion vs. static storage, and no extra organ shipping box is available to make a transfer of organ container 11 possible or if removal of organ container 11 is not desired. This may also be desirable should a leak develop in the coolant tank 291 or an individual coolant pack necessitating cooling material removal for correction of the leak. As a result, it may be advantageous to compartmentalize the cooling material into several packs rather than to allow the cooling material to exist as one continuous mass since a breach in coolant container would allow less cooling material to escape with the compartmentalized approach. Also this permits replacement of the coolant pack after a recommended period of use. Additionally, coolant replaceability would increase versatility of the device by permitting the use of multiple cooling materials. The user could for example switch from preserving one type of organ in favor of another organ and therefore use a different storage temperature without purchasing an entirely new organ shipping box. Finally, removability would permit coolant replacement when better materials are discovered that deliver the same storage temperatures previously achieved but are considerably less toxic or flammable, have longer lifetimes, and/or have considerably larger latent heats of fusion and/or lower densities for reducing overall organ shipping box weight. The illustration of the cooling material 226 as one contiguous block in FIG. 3 is for simplicity of illustration only.

Although Pegg (Cryobiology 11: 238–247, 1974) has shown that rabbit kidneys preserved by continuous perfusion at temperatures as high as 10° C. for periods as long as 48 hours do not require oxygen, an oxygenator can be provided for in the line 119 or 120. In operation, the oxygenator would mount in the pump assembly 240 and would be supplied by air derived from the exhaust of the muffler/power generator 235. The inclusion of an oxygenator would be an advantage also for pH control, since $CO_2$ would also be removed while $O_2$ was introduced. There is generally no need to increase oxygen tension to above that found in ordinary air for this application, and there is no likely need to include $CO_2$; however, the inclusion of small additional amounts of $O_2$ or $CO_2$ in the compressed air can be accomplished without difficulty if it is considered essential.

The organ pump assembly pack 240 can contain additional equipment. For example, a syringe pump may be included to permit programmed addition of a drug into the perfusate to benefit the organ or to carry out experiments on the effect of the drug. An oxygenator mount and connecting tube from the muffler 235 to the pack 240 can be provided.

Although the above-described arrangement for connecting the pressure sensing line to the pressure transducer is preferred since it involves no possibility of microbial contamination, if it is problematic for any reason, e.g., manufacturing difficulties, two alternatives are suggested. In the scheme illustrated in FIG. 9, the operator would unscrew a male Luer plug 284 from the female fitting 283 of the dome 282 preattached to pressure transducer 259, unscrew female cap 224 from the male Luer fitting 285 on the end of line 222, and then connect 285 to 283 and 284 to 224 as shown. This forms the desired sterile connection and conserves the sterility of cap 224 and plug 284 so that they can be re-used to replug their respective sites of origin when the organ is to be converted back to static storage. During perfusion, they can be kept in a snap-flap pouch provided on the inner wall of cover 245. Because it is possible that sterility will not be maintained for these components 224 and 284, sterile replacements may likewise be provided in a similar pouch, and sterilizing alcohol swabs and replacement domes 282 may also be provided in the event of any other contamination.

Figure 9A:
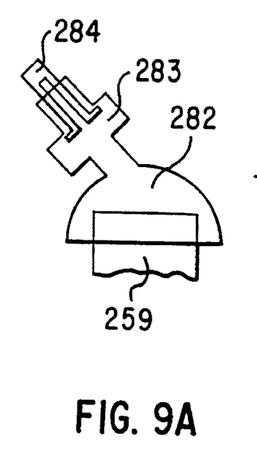
FIG. 9 depicts an alternative approach for connecting a pressure sensing line to a pressure transducer.
Figure 9B:
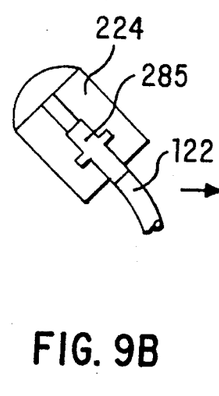
Figure 9C:
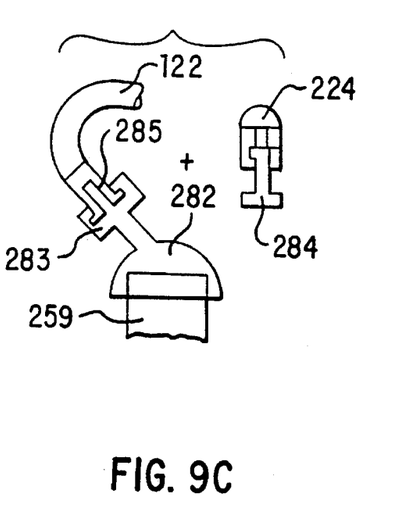

An alternative approach would be to connect cap 224 to site 283 using an intervening tube containing one or more sterile needles. Cap 224 would be swabbed with alcohol and pierced by the sterile needle leading to 283 to make a seal that could be reversed without loss of sterility by withdrawing the needle. The other end of the connecting tube could have a needle to pierce a similar diaphragm on site 283, or site 283 could come with the needle line pre-attached. Again, replacement needle connections could be provided.

The invention has been described with reference to embodiments thereof which are intended to be illustrative. Various changes and modifications may be made without departing from the spirit and scope of the invention as defined by the following claims.

What is claimed is:

1. A device for holding an organ, comprising:
   an organ container;
   a lower organ receiving portion located within the organ container; and
   an upper organ receiving portion located within the organ container and spaced from said lower organ receiving portion, wherein the upper and lower organ receiving portions are configured to contact and immobilize an organ.

2. The device of claim 1, wherein the organ container includes a cover, and further comprising:
   a temperature controlled portable storage module for receiving the organ container.

3. The device according to claim 2, wherein said storage module includes an outer wall and an inner wall, a cooling cavity between the outer wall and the inner wall that is adapted to receive a cooling material, and an organ container receiving cavity formed by the inner wall.

4. The device according to claim 3, further comprising cooling means for cooling a cooling material located within said cooling cavity.

5. The device according to claim 4, further comprising:
   a cover, the cover including a cover cooling cavity between outer and inner walls of the cover, wherein said cover cooling cavity is adapted to receive a cooling material.

6. The device according to claim 2, further comprising:
   a cooling cavity temperature monitor;
   an organ temperature monitor; and
   a display on said storage module operatively connected to said cooling cavity temperature monitor and said organ temperature monitor.

7. The device according to claim 6, further comprising a pH monitor for monitoring the pH of a perfusate fluid within said organ container, wherein said display is also operatively connected to said pH monitor.

8. The device according to claim 1, wherein said upper and lower organ receiving portions are padded.

9. The device according to claim 1, wherein said upper and lower organ receiving portions are inflatable.

10. The device of claim 2, wherein the portable storage module includes at least one vibration absorber mounted on the portable storage module.

11. The device according to claim 2, further comprising:
    portable perfusion means for circulating a perfusion fluid, wherein the perfusion means is removably attachable to an exterior of the portable storage module; and
    a perfusion fluid tube, wherein first and second ends of the perfusion fluid tube are in fluid communication with an interior of the organ container to form a closed fluid system, wherein the perfusion fluid tube is extendable from the organ container to an exterior of the portable storage module, and back to the organ container, and wherein the perfusion fluid tube is connectable to the perfusion means.

12. The device according to claim 3, wherein the cooling means comprises at least one cooling passageway that extends through the cooling cavity such that a coolant may be circulated through the cooling passageway to control the temperature of a cooling material in the cooling cavity.

13. The device according to claim 12, wherein the cooling means further comprises a container of compressed gas, wherein the container is attachable to the cooling passageway, and wherein gas from within the container may be expanded and circulated through the cooling passageway to control the temperature of a cooling material in the cooling cavity.

14. The device according to claim 4, wherein the cooling means comprises at least one cooling passageway that extends through the cooling cavity and the cover cooling cavity such that a coolant may be circulated through the cooling passageway to control the temperature of a cooling material in the cooling cavity and the cover cooling cavity.

15. A device for storing or transporting an organ comprising:
    an organ container having a cover, wherein the organ container also serves as a perfusate fluid reservoir;
    a temperature controlled portable storage module for receiving said organ container;
    portable perfusion means for circulating a perfusion fluid, wherein the perfusion means are removably attachable to an exterior of the portable storage module; and a perfusion fluid tube, wherein first and second ends of the perfusion fluid tube are in fluid communication with an interior of the organ container to form a closed fluid system, wherein the perfusion fluid tube is extendable from the organ container to an exterior of the portable storage module, and back to the organ container, and wherein the perfusion fluid tube is connectable to the perfusion means.

16. The device according to claim 15, wherein said portable storage module comprises:

inner and outer walls;

at least one closable passageway extending through the inner and outer walls and configured to accept the perfusion fluid tube; and at least one removable insert that is positionable within said at least one closable passageway when the perfusion fluid tube is not present in the at least one closable passageway.

17. The device of claim 15, wherein the organ container includes a first recess adjacent a position adapted to receive an organ; and wherein the portable storage module includes a first temperature sensor for sensing a temperature of an organ in the organ container, the first temperature sensor being mounted on the portable storage module such that the first temperature sensor is positioned within the first recess when the organ container is mounted on the portable storage module.

18. The device of claim 17, wherein the organ container further includes a second recess adjacent a perfusate fluid input port; and wherein the portable storage module further includes a second temperature sensor for sensing a temperature of a perfusate fluid in the organ container, wherein the second temperature sensor is mounted on the portable storage module such that the second temperature sensor is positioned within the second recess when the organ container is mounted on the portable storage module.

19. The device of claim 18, further comprising a display that is operatively connected to the first and second temperature sensors.

20. The device according to claim 15, further comprising:

pressure sensing means for sensing a fluid pressure in the perfusion fluid tube; and a controller operatively connected to the pressure sensing means and the perfusion means for controlling a perfusion rate of the perfusion means based on a fluid pressure in the perfusion fluid tube.

21. The device according to claim 15, further comprising at least one perfusate filter connected to said perfusion fluid tube.

* * * * *